(12) United States Patent
Marble

(10) Patent No.: US 8,591,471 B1
(45) Date of Patent: Nov. 26, 2013

(54) SECURE SELF ADHERING IV CATHETER ASSEMBLY

(76) Inventor: Benjamin Marble, Long Beach, MS (US)

( * ) Notice: Subject to any disclaimer, the term of this patent is extended or adjusted under 35 U.S.C. 154(b) by 247 days.

(21) Appl. No.: 12/693,350

(22) Filed: Jan. 25, 2010

(51) Int. Cl.
*A61M 5/32* (2006.01)
(52) U.S. Cl.
USPC .............................. 604/174; 604/180; 604/177
(58) Field of Classification Search
USPC .............. 604/180, 174, 177, 165.03; 206/364
See application file for complete search history.

(56) References Cited

U.S. PATENT DOCUMENTS

| | | | |
|---|---|---|---|
| 3,064,648 A | 11/1962 | Bujan | |
| 3,670,727 A | 6/1972 | Reiterman | |
| 4,324,236 A * | 4/1982 | Gordon et al. | 604/272 |
| 4,388,074 A | 6/1983 | Seberg et al. | |
| 4,676,783 A | 6/1987 | Jagger et al. | |
| 4,698,057 A | 10/1987 | Joishy | |
| 4,820,282 A | 4/1989 | Hogan | |
| 6,090,076 A | 7/2000 | Lane, Jr. | |
| 6,099,509 A | 8/2000 | Brown, Jr. et al. | |
| 6,809,230 B2 | 10/2004 | Hancock et al. | |
| 6,892,881 B2 * | 5/2005 | Leitch | 206/364 |
| 7,544,186 B2 * | 6/2009 | Davis et al. | 604/180 |
| 7,981,087 B2 * | 7/2011 | Gesler, III | 604/174 |
| 2009/0326474 A1 * | 12/2009 | Bierman et al. | 604/180 |

FOREIGN PATENT DOCUMENTS

| | | |
|---|---|---|
| GB | 1 243 576 | 5/1969 |
| WO | WO00/15290 | 3/2000 |
| WO | WO2004/026389 | 4/2004 |

* cited by examiner

*Primary Examiner* — Kevin C Sirmons
*Assistant Examiner* — Deanna K Hall
(74) *Attorney, Agent, or Firm* — Michael I. Kroll

(57) ABSTRACT

A catheter assembly having a catheter with a longitudinal body having a transverse attachable detachable fastening member thereunder comprising a pliable polymeric element having a top side and a bottom side with the top side having a longitudinal groove fixedly attached to the catheter's longitudinal body with the bottom side having an adhesive layer covered by a peelably removable cover so that when removed the catheter assembly can be adhesively attached to a recipient's skin and when desirous of removal can be peelably removed from said recipient's skin.

6 Claims, 9 Drawing Sheets

SECURE SELF ADHERING IV CATHETER ASSEMBLY

BACKGROUND OF THE INVENTION

1. Field of the Invention

The present invention relates generally to catheters and, more specifically, to a catheter assembly wherein said catheter assembly comprises a catheter having a pair of transverse wings extending therefrom forming an integral part therewith. Each of the transverse wings has a top side and a bottom side with the bottom sides having an adhesive layer with a peelably removable cover.

The present invention also provides a catheter assembly having a catheter with a longitudinal body having a transverse attachable detachable fastening member thereunder comprising a pliable polymeric element having a top side and a bottom side with the top side having a longitudinal groove fixedly attached to the catheters longitudinal body with the bottom side having an adhesive layer covered by a peelably removable cover so that when removed the catheter assembly can be adhesively attached to a recipient's skin and when desirous of removal can be peelably removed from said recipient's skin.

Also provided are removal tabs, which are flexible tab end portions having no adhesive providing easy removal of the flexible tabs using one hand.

2. Description of the Prior Art

There are other catheter device designed for medical use. Typical of these is U.S. Pat. No. 3,064,648 issued to Bujan on Nov. 20, 1962.

Another patent was issued to Reiterman on Jun. 20, 1972 as U.S. Pat. No. 3,670,727. Yet another U.S. Pat. No. 4,388,074 was issued to Seberg et al. on Jun. 14, 1983 and still yet another was issued on Jun. 30, 1987 to Jagger et al. as U.S. Pat. No. 4,676,783.

Another patent was issued to Joishy on Oct. 6, 1987 as U.S. Pat. No. 4,698,057. Yet another U.S. Pat. No. 4,820,282 was issued to Hogan on Apr. 11, 1989. Another was issued to Lane, Jr. on Jul. 18, 2000 as U.S. Pat. No. 6,090,076 and still yet another was issued on Aug. 8, 2000 to Brown, Jr. et al. as U.S. Pat. No. 6,099,509.

Another patent was issued to Hancock et al. on Oct. 26, 2004 as U.S. Pat. No. 6,809,230. Yet another U.K. Patent No. GB1243576 was published to Abbott Laboratories on Aug. 18, 1971. Another was published to Howell on Sep. 14, 1999 as International Patent Application Publication No. WO 00/15290 and still yet another was published on Apr. 1, 2004 to Scofield as International Patent Application Publication No. WO 2004/026389.

U.S. Pat. No. 3,064,648

Inventor: Albert F. Bujan

Issued: Nov. 20, 1962

An intravenous needle assembly comprising a hollow needle having a pointed end, and a pair of oppositely extending semi-flexible wing sections connected to said hollow needle, each wing section having a weakened portion adjacent to and substantially parallel with said hollow needle.

U.S. Pat. No. 3,670,727

Inventor: Donald R. Reiterman

Issued: Jun. 20, 1972

A medical infusion set for administering parenteral liquid into a patient's veins in which the set is in the form of a continuous flexible loop that is manually broken apart before venipuncture at a frangible section (this section comprising an indication of the sterile integrity of the set to subsequent users), the set providing means for flushing air therefrom while maintaining the set in a sterile condition by either running the liquid through the loop before effecting the venipuncture, or flushing the air from the set by using the patient's blood flowing therethrough and before connection to the liquid being administered; the set including means protecting either a connector to the parenteral liquid or the needle against contamination while air is flushed from the set; and the needle of the set including a pair of flexible plastic wings generally diametrically opposed and including manually interengageable portions comprising interengageable upstanding ribs manually interlockable when manually pinched together to form a dual purpose temporary handle in which the wings can be subsequently spread apart adjacent the venipuncture in the patient for securement to the patient to stabilize the implanted needle or cannula.

U.S. Pat. No. 4,388,074

Inventor: Charles H. Seberg

Issued: Jun. 14, 1983

A needle-inside, catheter placement assembly including needle and catheter units. The needle unit comprises a needle joined by a flexible line to a needle hub. The catheter unit comprises a catheter, winged catheter insertion means, flexible tubing and tube hub, wherein an area of reduced thickness on each wing of the insertion means provides improved flexibility for the wing. The needle is captured within the winged catheter insertion means when the wings are simultaneously held in a vertical position and axial and rotational alignment of the needle and catheter units are maintained by mechanically interlocked complementary means associated with the needle and lumen of the winged catheter insertion means.

U.S. Pat. No. 4,676,783

Inventor: Janine C. Jagger et al.

Issued: Jun. 30, 1987

An intravenous needle with a sharpened distal end has a proximal end fixed within a first enlarged end of an inner tube. The enlarged end of the inner tube is held tightly within a first end of an outer tube by friction. The needle passes through a constricted opening in the first end of the outer tube. The second end of the inner tube passes through a constricted opening in the second end of the outer tube. The needle is used by gripping soft plastic wings on the outer tube and removing a needle cover from a nipple on the first end of the outer tube. The needle is then inserted in the desired location and the outer tube and a protruding end of the inner tube are taped in place. Fluids are permitted to flow through the inner tube and needle. When use is complete, the needle is removed from the vein, the protruding end of the inner tube is pulled outward, pulling the first end of the inner tube and the needle into the outer tube. The first end of the inner tube tightly wedges within the second end of the outer tube, holding the needle totally within the outer tube. Finally, the retracted used needle assembly is discarded, encased in the outer tube.

U.S. Pat. No. 4,698,057

Inventor: Suresh K. Joishy

Issued: Oct. 6, 1987

An assembly of built-in dual system for rapidly stabilizing and firmly securing an intravascular needle or catheter like instrument to a patient is disclosed. One portion of the system consists of a roll of adhesive tape fixed strategically in a wing like structure on each side of the needle or catheter. The second system is composed of built-in suction cups undersurface of a wing like structure on each side of the needle or catheter. Upon insertion of the needle, in a blood vessel of a patient, merely dabbing the wings of the catheter to the skin extrudes air out of the suction cups. Thus vacuum created causes the suction cups to cling to the skin immediately due to atmospheric pressure. As a result the wings and the needle are stabilized immediately. This frees the hands of the operator to uncoil the adhesive tape roll provided with a clip and handle device for easy grip. Each wing is taped down firmly to the skin, achieving permanent securement to the patient.

U.S. Pat. No. 4,820,282

Inventor: J. Martin Hogan

Issued: Apr. 11, 1989

A sheath for use in removing hypodermic needles having butterfly-shaped gripping side strips from patients and retaining the point of the removed needle in the sheath even when the needle and sheath are disposed of so that all persons who handle the needle are protected from being pricked.

U.S. Pat. No. 6,090,076

Inventor: Eugene Lane, Jr.

Issued: Jul. 18, 2000

A prepared kit according to the invention includes a plurality of pre-cut tape strips for securing a medical device such as a catheter, an intravenous needle, tubing, or a similar device to a patient's skin or to a support. Once a medical attendant has inserted a medical device into a patient's skin at an insertion site, the attendant secures the medical device to the patient's skin or to a support at a point spaced from the insertion site by engaging the medical device with a portion of each of the strips. Each of the strips has a biocompatible adhesive on one surface and a non-adhesive portion on the opposite surface, such that medical personnel are able to rapidly and effectively secure the medical device when putting the device into use. The kit can further include the following: a sterilized pad to provide protective padding for the patient's skin; an alcohol wipe for sterilizing the patient's skin prior to inserting the medical device; and a medical device such as an intravenous needle. Each tape strip can have a layer of peelable release paper adhering to the adhesive surface of the tape strip. One end of the layer of peelable release paper extends beyond an edge of the adhesive surface of the tape strip creating a tab. The tab allows a medical attendant to quickly and easily remove the release paper and place the tape strip to secure the medical device without having to remove protective plastic gloves, place the tape strips on an unsterilized surface, or employ scissors and a tape roll.

U.S. Pat. No. 6,099,509

Inventor: William S. Brown, Jr. et al.

Issued: Aug. 8, 2000

A kit for disposing of a contaminated I.V. needle and delivering adhesive wound dressings to a patient with preferably a single gloved hand includes an adhesive mounting substrate to attach the apparatus to an available surface. An adhesive needle sheath carrier extends from the base of the apparatus for securing a needle and needle sheath for disposal following use. To the base of the apparatus are releasably adhered a wound barrier and taping strips to aid in securing a catheter to a patient. Tabs are provided on the wound barrier and taping strips to facilitate their removal from the base of the apparatus. The apparatus allows a medical technician to insert a catheter into a patient and maintain pressure on the catheter at the wound site with one hand, while disposing of the contaminated needle and then securing the catheter with wound dressings, all with preferably a single gloved other hand, thereby reducing the incidence of infection or injury.

U.S. Pat. No. 6,809,230

Inventor: Betty Hancock et al.

Issued: Oct. 26, 2004

A transparent cover for a venipuncture site providing a transparent window to view the status of the catheter, skin and puncture site and to protect that site from exposure to water, germs and other contaminants. The cover is comprised of one piece of flexible transparent material which conforms to the contour of the skin and has a main body foldably attached to an arm. The arm is adhesively attached behind the catheter to the skin, while the main body is folded on top of the arm and adhesively attached on one side to the arm and to the catheter lying on top of the arm and on its other sides to the skin. A method for applying and removing the cover is also disclosed.

U.K. Patent Number GB1243576

Inventor: Abbott Laboratories

Published: Aug. 18, 1971

A catheter assembly comprises a catheter 2 with a hub 3 enclosing a needle with a hub 5, a flexible wing assembly 1 on said catheter and a catheter sheath 7. The wing assembly has two wings 8, 9, and an intermediate housing 10 with an axial aperture 28 to receive the catheter 2, and struck-out portions (29, 30, 31, FIG. 5) such that when the wings are brought up from the usual position (FIG. 8) to the venipuncture position (FIG. 9, not shown), or laid flat for attachment to the patient after insertion (FIG. 10, not shown), the catheter is pinched so as to be axially immovable in the intermediate housing 10. A forward portion (24, FIG. 4) of the needle hub 5 is enclosed by the catheter hub 3, and the needle sheath 7 has on its proximal end 20 an extension (21), FIG. 3 (not shown) with a U-shaped section (22) having inwardly projecting ribs 23 which engage portion 25 of the catheter hub forward section. The needle hub 5 has a reduced diameter rear portion 14 which receives an air vent 15, which includes a glass fibre filter which allows air but not blood to escape. Wings 8, 9 are coated on their under surfaces with adhesive for fixing to the patient, which adhesive is protected by strips 32.

International Patent Application Publication No. WO 00/15290

Inventor: Glade H. Howell et al.

Published: Mar. 23, 2000

A winged catheter introducer for use in introducing a catheter into a blood vessel is disclosed. A needle is disposed within the catheter to help penetrate a patient's blood vessel. The needle and catheter are disposed within an introducer body having a pair of deformable wings extending from opposite sides of the body. A pair of opposing clamp jaws are disposed within the introducer body adjacent the wings. The clamp jaws are configured to grip and retain the catheter and needle when the wings are compressed towards each other. In a disclosed embodiment, the clamp jaws are biased in an open configuration and define clamp surfaces having angled ridges which engage the catheter exterior surface.

International Patent Application Publication No. WO 02/026389

Inventor: Judith A. Scofield

Published: Apr. 1, 2004

A dressing is disclosed for use with a catheter assembly. Such catheter assemblies may include a catheter hub with a side port extending from the catheter hub and wings extending laterally from the catheter hub. In the dressing, a transparent dressing sheet has a substantially square profile and a notch disposed along at least one side of the profile. A release liner has a substantially square profile and a liner handle extending beyond the square profile of the liner. The release liner is removably engaged to the dressing sheet. A reinforcement material has a center portion and arms extending along the center portion. The center portion is positioned at one corner of the dressing sheet and the arms extend along at least two side of the square profile of the dressing sheet. A material notch is disposed along at least one side of the square profile of the material. The material notch is aligned with the dressing sheet notch. The center portion has a distal edge matching the shape of the distal edge of the wings of the catheter hub. A stiffening frame is releasably attached to the dressing sheet and has a substantially square cross section and a center aperture that exposes at least that portion of the dressing sheet disposed between the arms of the reinforcement material.

While these needle assemblies may be suitable for the purposes for which they were designed, they would not be as suitable for the purposes of the present invention, as hereinafter described.

SUMMARY OF THE PRESENT INVENTION

A primary object of the present invention is to provide a catheter assembly that can be adhesively attached to a recipient's skin.

Another object of the present invention is to provide a catheter assembly having a longitudinal body with transverse tabs extending therefrom.

Yet another object of the present invention is to provide a catheter assembly wherein said transverse tabs are an integral part of said catheter assembly.

Still yet another object of the present invention is to provide a catheter assembly wherein said tabs are manufactured of a pliable polymeric material.

An additional object of the present invention is to provide a catheter assembly wherein said tabs have a top side and a bottom side with an adhesive layer covering said bottom side.

A further object of the present invention is to provide a catheter assembly wherein said adhesive layer is covered by a peelably removable cover.

A yet further object of the present invention is to provide a catheter assembly having a longitudinal body with a transverse pliable member.

A still yet further object of the present invention is to provide a catheter assembly wherein said transverse member has a longitudinal groove for fixedly attaching the catheter thereto.

Another object of the present invention is to provide a catheter assembly wherein said transverse member has a top side and a bottom side with the bottom side having an adhesive layer.

Yet another object of the present invention is to provide a catheter assembly wherein said transverse member's adhesive layer has a peelably removable cover thereover.

Additional objects of the present invention will appear as the description proceeds.

The present invention overcomes the shortcomings of the prior art by providing a catheter assembly comprising a catheter having a pair of transverse wings extending therefrom forming an integral part therewith. Each of the transverse wings has a top side and a bottom side with the bottom sides having an adhesive layer with a peelably removable cover. The present invention additionally provides a catheter assembly having a catheter with a longitudinal body having a transverse attachable detachable fastening member thereunder comprising a pliable polymeric element having a top side and a bottom side with the top side having a longitudinal groove fixedly attached to the catheter's longitudinal body with the bottom side having an adhesive layer covered by a peelably removable cover so that when removed the catheter assembly can be adhesively attached to a recipient's skin and when desirous of removal can be peelably removed from said recipient's skin.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
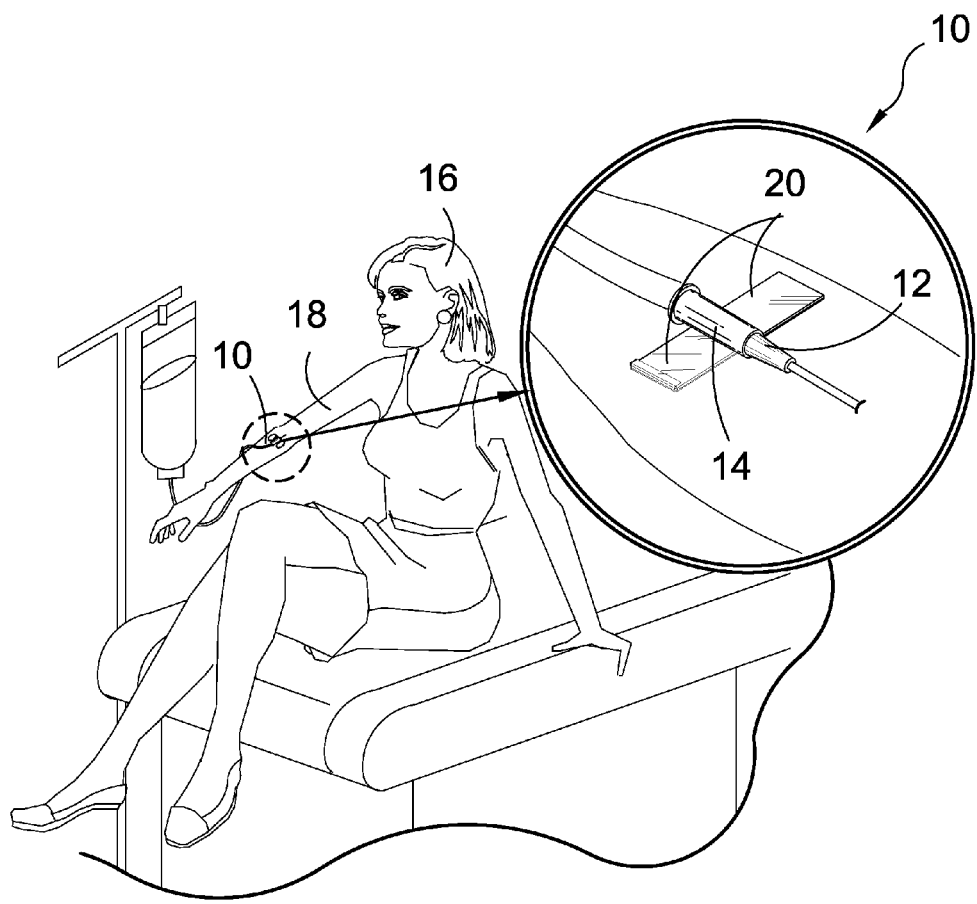
FIG. 1 is an illustrative view of the present invention in use.

Turning now descriptively to the drawings, in which similar reference characters denote similar elements throughout the several views, the figures illustrate the Secure Self Adhering IV/Catheter Assembly of the present invention. With regard to the reference numerals used, the following numbering is used throughout the various drawing figures.

10 Secure Self Adhering IV/Catheter Assembly
12 catheter
14 housing
16 user
18 arm of 16
20 flexible tab
22 removal tab
24 longitudinal groove
26 adhesive coating
28 peel away sheet
30 needle cannula
32 pliable transverse sheet
34 sterile hermetically sealed package

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

FIG. 1 is an illustrative view of the present invention in 10 use. Shown is the catheter assembly 10 comprising a device for aiding in the setup of a transdermal catheter 12 or IV. Shown is the catheter body 14 attached to the user's 16 arm 18 via a flexible tab 20 having a non shear adhesive joining the device to the user. This adhesive allows for the technician to more efficiently set up a catheter or IV for a patient.

Figure 2:
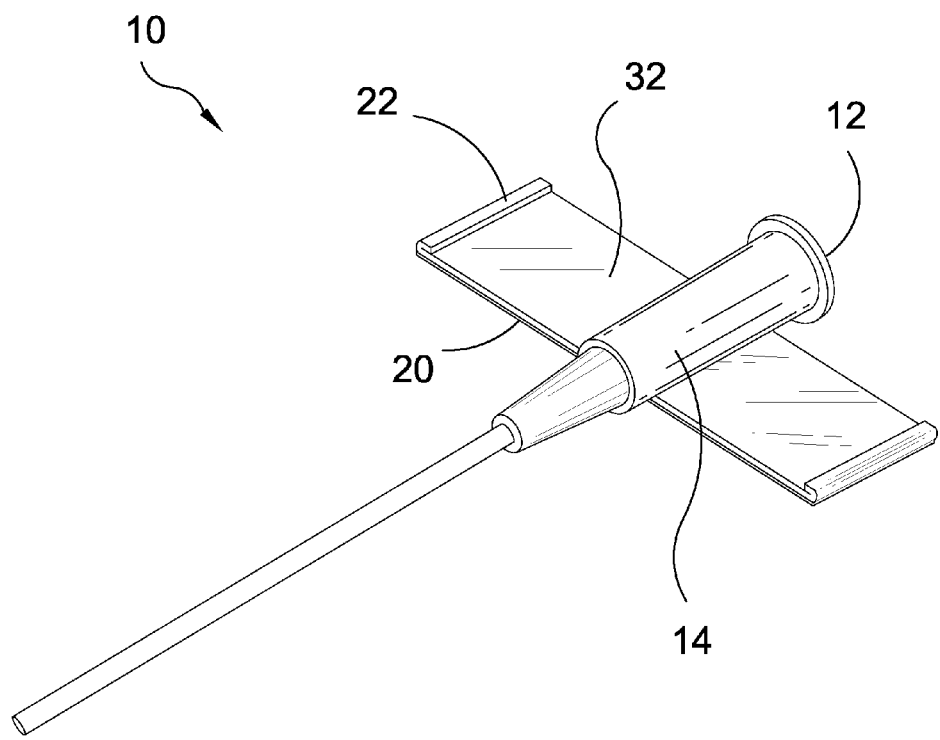
FIG. 2 is an illustrative view of the present invention.

FIG. 2 is an illustrative view of the present invention 10. Shown is the present invention, a device for aiding in the setup of a transdermal catheter 12 or IV having a pliable transverse sheet 32 divided into a pair of flexible tabs 20 to aid in the attachment of the catheter body 14 to a patient's arm and a removal tab 22 providing for single hand removal when desired.

Figure 3:
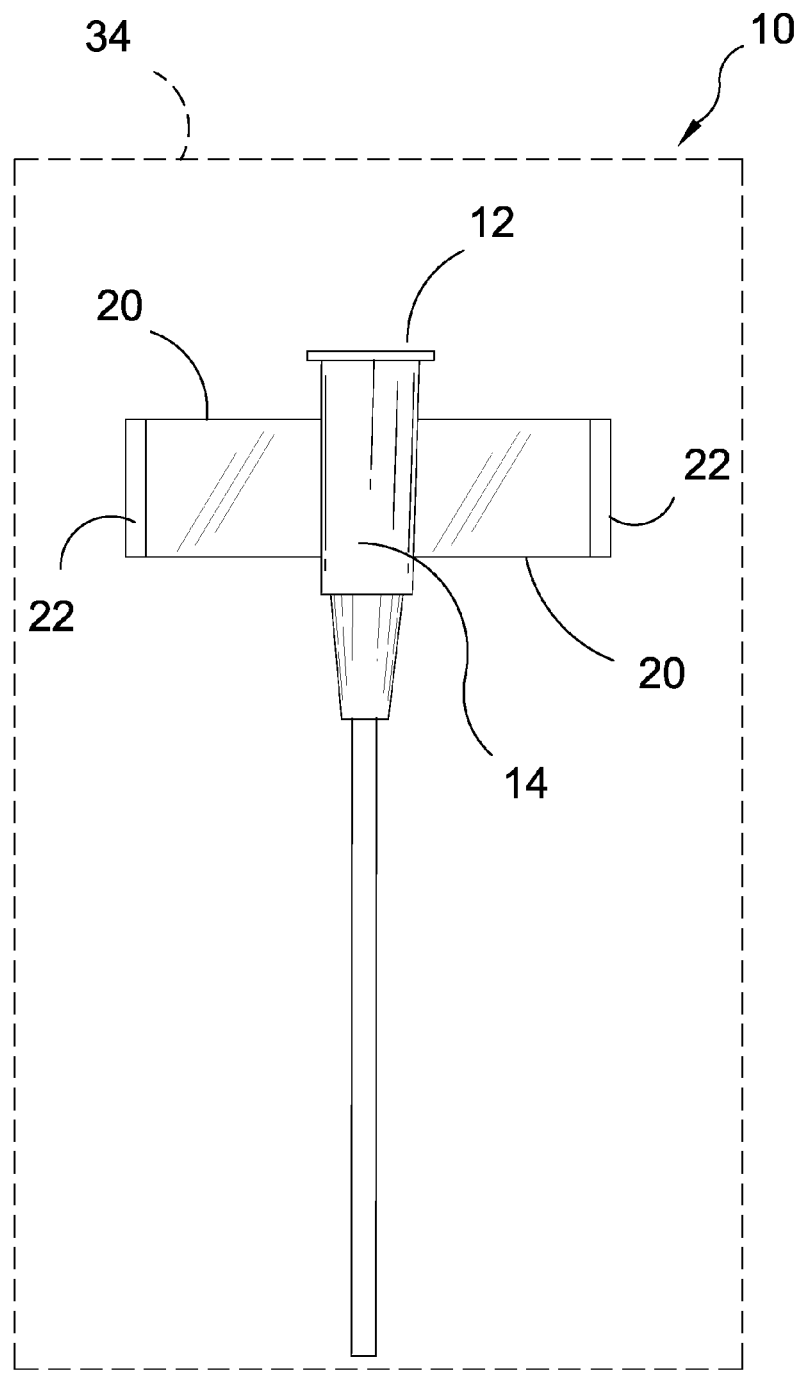
FIG. 3 is a top view of the catheter assembly of the present invention.

FIG. 3 is a top view of the catheter assembly of the present invention 10. Shown is the catheter assembly 10 having a catheter 12 with an adhesive flexible tab 20 integral with the body 14 utilized to aid in the attachment of the catheter assembly 10 to a patient's skin and a removal tab 22 providing for single hand detachment of the catheter assembly when desired. The catheter assembly 10 is packaged in a sterile, hermetically sealed package 34 upon completion of manufacture.

Figure 4:
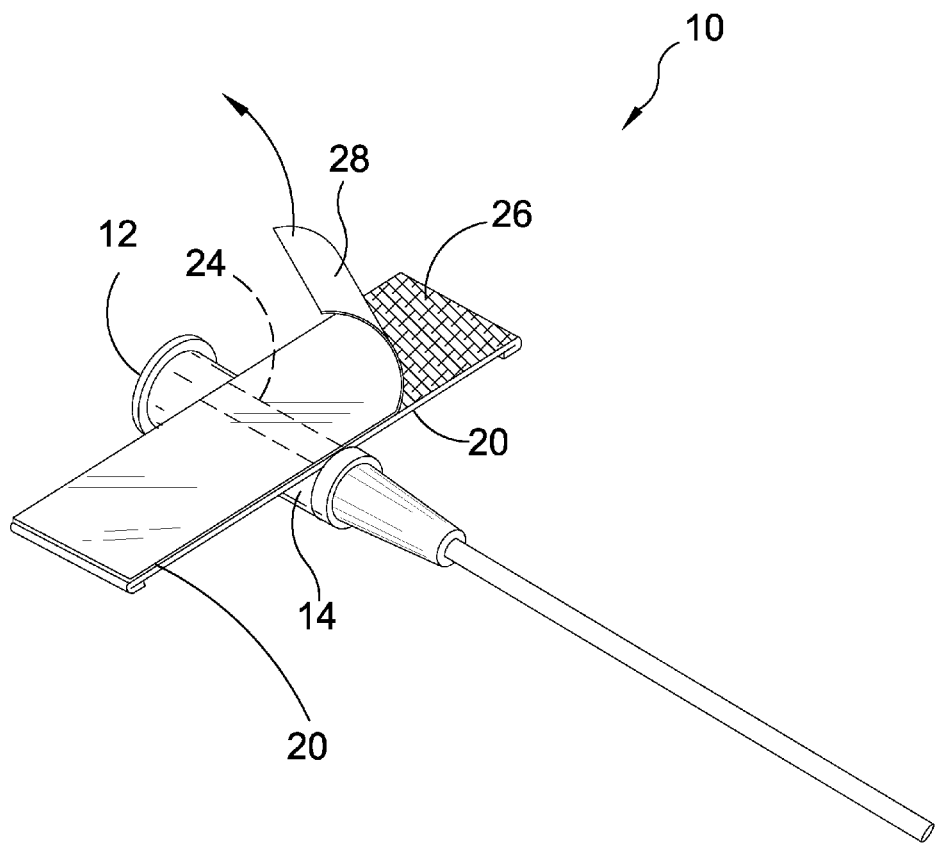
FIG. 4 is a perspective view of the present invention.

FIG. 4 is a perspective view of the present invention 10. Shown is the catheter assembly 10 with an integral tab 20 with an adhesive 26 coated bottom with a protected peel away sheet 28 exposes the adhesive 26 when removed to aid in the attachment of the catheter assembly 10 to a patient's skin. The catheter 14 is seated and bonded to a longitudinal groove 24 to provide a greater contact area during manufacture.

Figure 5:
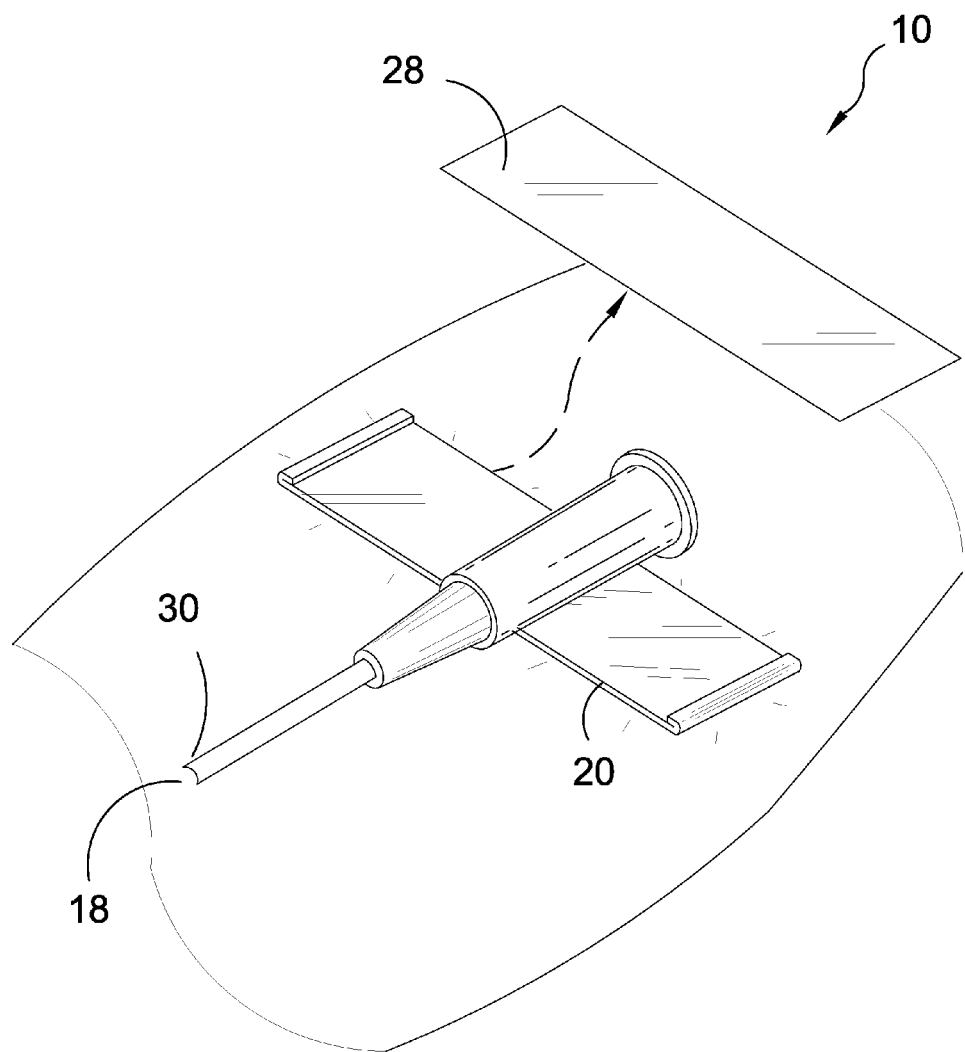
FIG. 5 is an illustrative view of the catheter assembly in use.

FIG. 5 is an illustrative view of the catheter assembly 10 in use. Shown is the catheter assembly 10 of the present invention being applied to a patient's arm 18, prior to or subsequently after the needle cannula 16 is inserted into the vein the peelable sheet material 28 is removed from the flexible tabs 20 to expose the adhesive.

Figure 6:
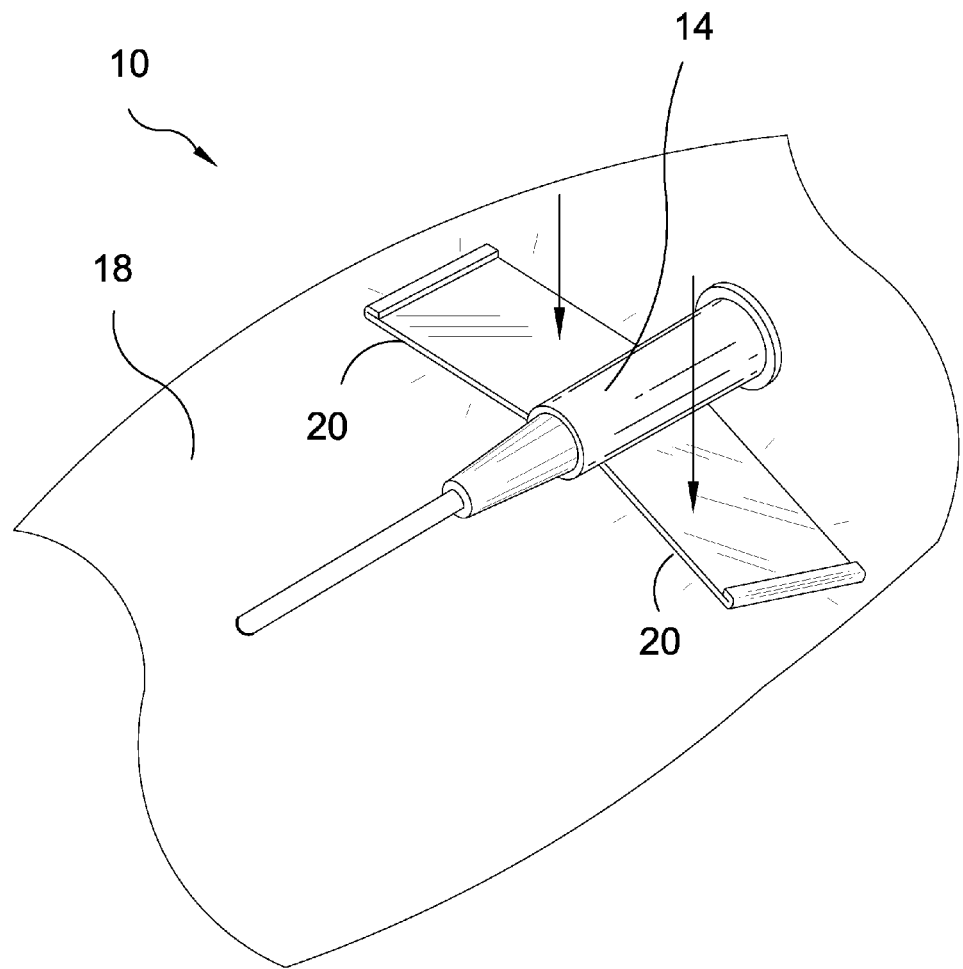
FIG. 6 is an illustrative view of the catheter assembly in use.

FIG. 6 is an illustrative view of the catheter assembly 10 in use. Shown is the catheter assembly 10 applied to a patient's arm 18. Once the peelable sheet is removed pressure over the flexible tabs 20 are all that is needed to bind the catheter body 14 to the patient's arm 18.

Figure 7:
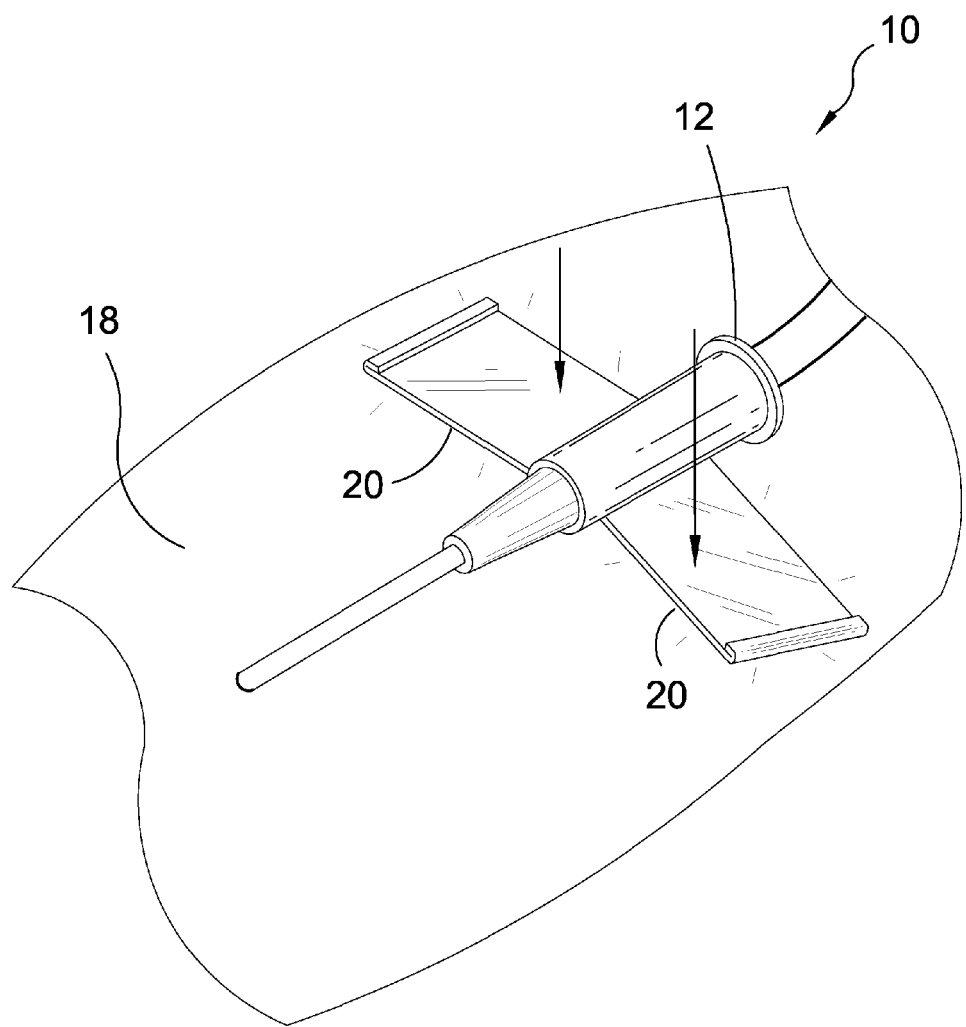
FIG. 7 is an illustrative view of the present invention in use.

FIG. 7 is an illustrative view of the present invention 10 in use. Shown is the present invention 10 applied to a patient's arm 18. Once the flexible tabs 20 are secured to the patient's arm the catheter 12 may be attached and additional dressings applied.

Figure 8:
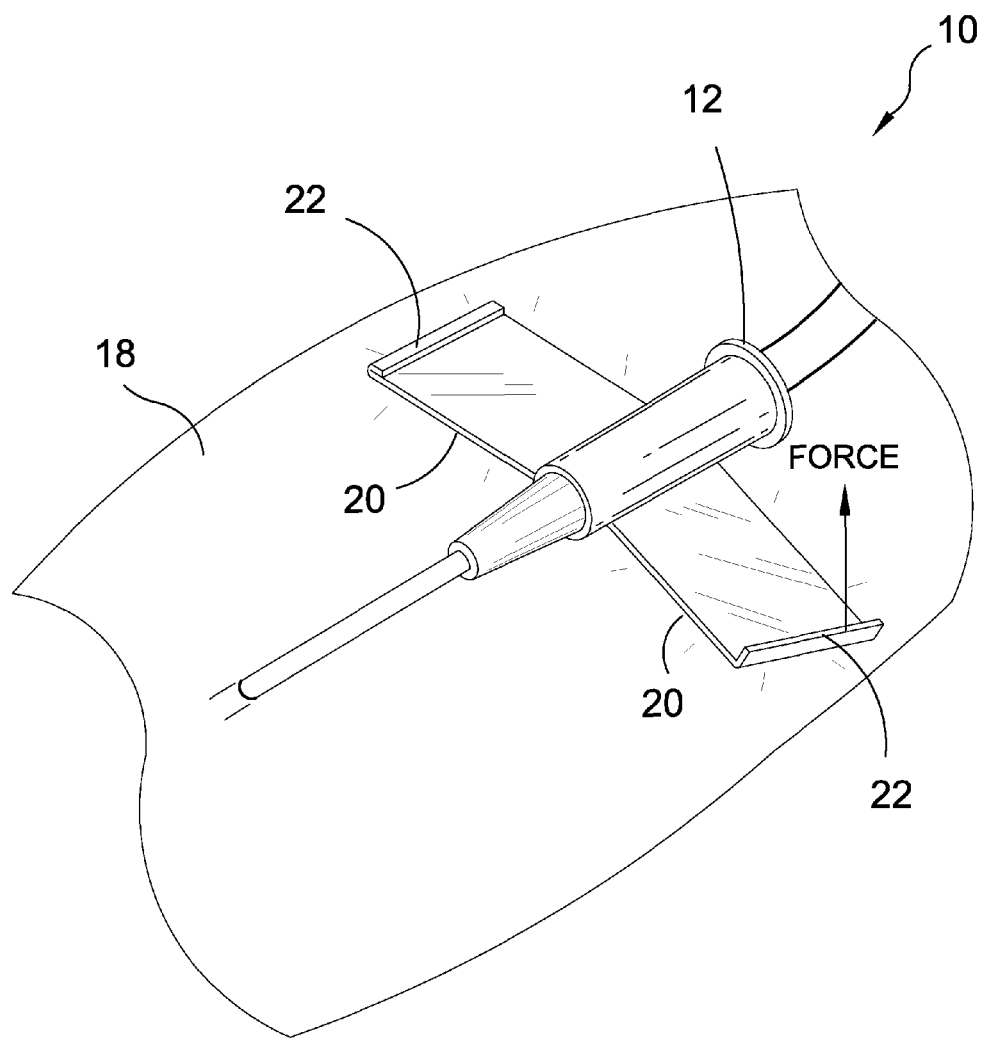
FIG. 8 is an illustrative view of the catheter assembly in use.

FIG. 8 is an illustrative view of the catheter assembly 10 in use. Shown is the catheter assembly 18 adhesively attached to a user 18 having a removal tab 22 on each end of the flexible tabs 20 so that the catheter 12 can be detached therefrom using one hand by grasping the removal tab 22 and pulling one or both tabs in turn. The removal tabs 22 have no adhesive on either surface and are simply portions provided for easily grasping the flexible tab end for single handed removal.

Figure 9:
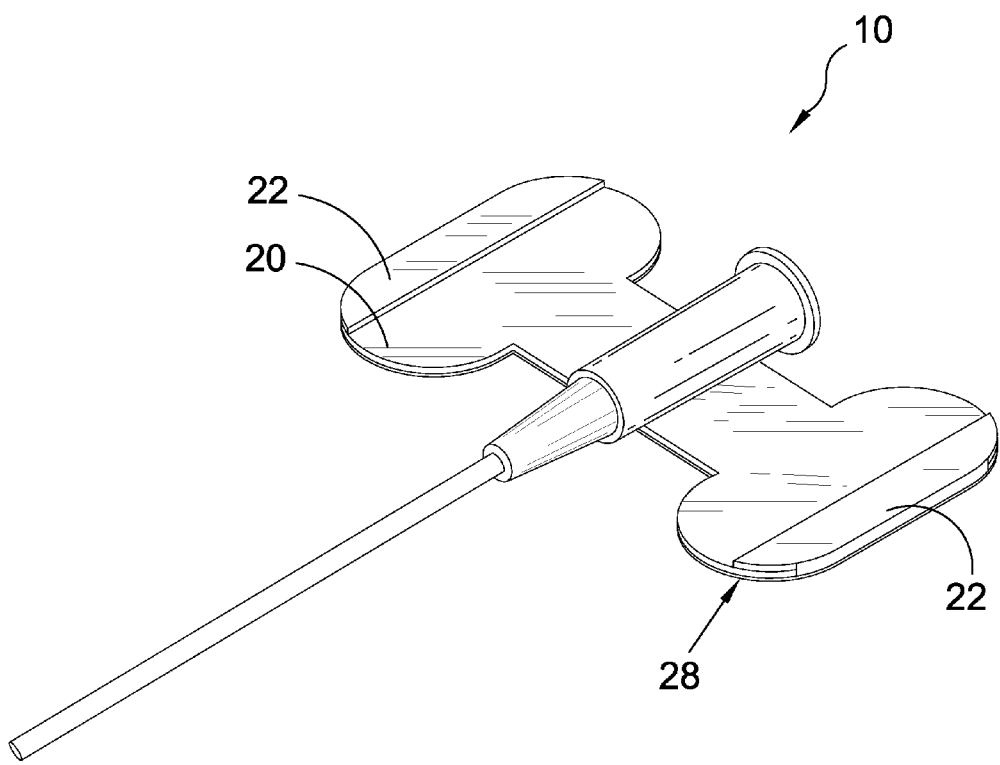
FIG. 9 is an additional element of the present invention in use.

FIG. 9 is an additional element of the present invention 10 in use. Shown is the present invention having a single flexible tab 20 having an adhesive layer and peel away sheet 28. A single flexible element may be utilized in order to simplify the process of peeling only one strip as opposed to two.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:
1. A self-adhering IV/catheter assembly comprising:
 a) a catheter having a main body portion;
 b) a transverse flexible sheet rectangular in shape with squared distal edges having a top side and an underside medially secured to a bottom side of said catheter body and projecting from opposing sides of said body portion;

c) a releasable adhesive coating on the underside of said transverse flexible sheet for adhering said assembly directly to the skin of a patient;

d) said transverse flexible sheet including a central groove disposed medially on said top side for receiving directly a bottom portion of said body of said catheter to provide an extended contact surface for bonding during manufacturing of said assembly and each said distal edge having a folded over removal tab lining a full length of said distal edge for single hand detachment of the catheter assembly when desired; and d) said catheter with said transverse flexible sheet attached thereto during manufacture packaged within a sterile, hermetically sealed package ready for use as a complete assembly whereby said transverse flexible sheet is integral with said catheter body and allowing said catheter assembly to be applied directly without any intermediary.

2. The self-adhering IV/catheter assembly according to claim 1, wherein the adhesive coating is protected until ready for usage by a peel away sheet.

3. The self-adhering IV/catheter assembly according to claim 2, wherein said catheter further comprises a needle cannula extending linearly from said body.

4. The self-adhering IV/catheter assembly according to claim 3, wherein said removal tabs are adhesive free.

5. The self-adhering IV/catheter assembly according to claim 3, wherein said transverse flexible sheet is comprised of a pliable polymeric element.

6. A method of securing and releasing a self-adhering IV/catheter assembly to a patient's target skin surface consisting of the steps of:

a) providing a catheter having a body and a needle;

b) providing a transverse sheet rectangular in shape with squared distal edges and comprised of a pliable polymeric material having an upper side and an underside with said upper side having a groove disposed in a medial portion thereof and only said underside having a releasable adhesive coating and protective peel-off sheet disposed thereon;

c) bonding said catheter body within said groove of said pliable transverse sheet with said transverse sheet projecting from both sides from a bottom portion of said catheter body, each said distal edge having a folded over removal tab lining a full length of said distal edge for single hand detachment of the catheter assembly when desired;

d) packing said catheter assembly with said catheter body attached to said transverse sheet into a sterile hermetically sealed container followed by delivery, transport to and storage at a place of use;

e) removing said catheter assembly with attached transverse sheet from said container when ready for use;

f) inserting said needle into said patient's desired blood vessel;

g) removing said protective peel off sheet to expose said adhesive coating;

h) applying a bias against said flexible tabs to form a releasable bond between said tabs and said patients skin without use of any intermediate apparatus;

i) removing said assembly upon completion of the procedure by grasping said removal tab and pulling it up thereby releasing from the user's skin; and j) disposing of said catheter assembly in an appropriate manner.

* * * * *